US008077917B2

(12) United States Patent
Forsgren

(10) Patent No.: US 8,077,917 B2
(45) Date of Patent: Dec. 13, 2011

(54) SYSTEMS AND METHODS FOR ENHANCING IMAGES IN A VIDEO RECORDING OF A SPORTS EVENT

(76) Inventor: Daniel Forsgren, Stockholm (SE)

(*) Notice: Subject to any disclaimer, the term of this patent is extended or adjusted under 35 U.S.C. 154(b) by 1030 days.

(21) Appl. No.: 11/917,741

(22) PCT Filed: Jun. 22, 2006

(86) PCT No.: PCT/SE2006/050214
§ 371 (c)(1),
(2), (4) Date: Dec. 14, 2007

(87) PCT Pub. No.: WO2007/004974
PCT Pub. Date: Jan. 11, 2007

(65) Prior Publication Data
US 2008/0199043 A1  Aug. 21, 2008

(30) Foreign Application Priority Data
Jul. 1, 2005 (SE) ........................ 0501549

(51) Int. Cl.
*G06K 9/00* (2006.01)
*H04N 7/18* (2006.01)
(52) U.S. Cl. ........................ 382/103; 348/157
(58) Field of Classification Search .......................... None
See application file for complete search history.

(56) References Cited

U.S. PATENT DOCUMENTS

| 5,342,051 A | 8/1994 | Rankin et al. |
|---|---|---|
| 5,413,345 A | 5/1995 | Nauck |
| 5,489,099 A | 2/1996 | Rankin et al. |
| 5,798,519 A | 8/1998 | Vock et al. |
| 5,912,700 A | 6/1999 | Honey et al. |
| 5,938,545 A | 8/1999 | Cooper et al. |
| 5,953,056 A * | 9/1999 | Tucker ........................ 348/157 |
| 6,233,007 B1 | 5/2001 | Carlbom et al. |

(Continued)

FOREIGN PATENT DOCUMENTS
WO      9728856      8/1997
(Continued)

OTHER PUBLICATIONS
International Search Report for PCT/SE2006/050214.
(Continued)

*Primary Examiner* — Jingge Wu
*Assistant Examiner* — Tahmina Ansari
(74) *Attorney, Agent, or Firm* — Moore & Van Allen PLLC; W. Kevin Ransom

(57) ABSTRACT

A video signal representing rapid ball movement is produced from a series of source images. An initial image position for the moving ball is identified by, for each image, producing a difference image between sequential images. In the difference image, image elements representing a contents alteration below a threshold are allocated a first value, and those representing a contents alteration above or equal to the threshold are allocated a second value. A set of candidates is then identified, where each candidate is represented by a group of neighboring image elements that all contain the second value. The group must fulfill a ball size criterion. A ball selection algorithm selects an initial image position from the set of ball candidates. The ball is tracked, and a composite image sequence is generated wherein a synthetic trace representing the path of the moving ball is shown as successively added image data.

22 Claims, 4 Drawing Sheets

U.S. PATENT DOCUMENTS

| | | | |
|---|---|---|---|
| 6,236,940 B1 | 5/2001 | Rudow et al. | |
| 6,449,010 B1* | 9/2002 | Tucker | 348/157 |
| 6,520,864 B1 | 2/2003 | Wilk | |
| 7,843,510 B1* | 11/2010 | Ayer et al. | 348/584 |
| 2003/0103648 A1* | 6/2003 | Ito et al. | 382/103 |
| 2004/0136592 A1* | 7/2004 | Chen et al. | 382/190 |
| 2004/0258154 A1* | 12/2004 | Liu et al. | 375/240.16 |
| 2005/0040710 A1* | 2/2005 | Ahn | 307/10.1 |
| 2008/0175441 A1* | 7/2008 | Matsumoto et al. | 382/107 |
| 2008/0199043 A1* | 8/2008 | Forsgren | 382/103 |
| 2009/0225845 A1* | 9/2009 | Veremeev et al. | 375/240.16 |
| 2009/0245571 A1* | 10/2009 | Chien et al. | 382/103 |

FOREIGN PATENT DOCUMENTS

| | | |
|---|---|---|
| WO | 9728856 A1 | 8/1997 |

OTHER PUBLICATIONS

International Preliminary Report on Patentability for PCT/SE2006/050214.

* cited by examiner

SYSTEMS AND METHODS FOR ENHANCING IMAGES IN A VIDEO RECORDING OF A SPORTS EVENT

THE BACKGROUND OF THE INVENTION AND PRIOR ART

The present invention relates generally to automatic image enhancement in connection with registration of moving images of a sports scene. More particularly the invention relates to a system according to the preamble of claim 1 and a method of producing a video signal according to the preamble of claim 10. The invention also relates to a computer program according to claim 22 and a computer readable medium according to claim 23.

Recording and broadcasting of sporting events is becoming an increasingly important market area, and therefore the competition is intensified to provide the viewers with satisfying experiences of such events. However, in some sports it is difficult to adequately reflect all important aspects of the game, for instance in a TV transmission. Golf and baseball are two examples of sports wherein a relatively small ball often travels over a comparatively large distance during a short period of time. Due to the technical limitations of the transmission medium and the cameras used it may be problematic for the viewers to follow the balls' path, and thus fully appreciate the sportsmen's performances.

In golf, for example, already after 30 to 70 meters flight an outgoing ball becomes so small that it is equivalent to less than one pixel of a conventional TV screen. Of course, this renders it very difficult to distinguish the ball, particularly if the white ball moves in front of a bright sky. In most cases, the sky is brighter than the rest of the image, i.e. the golfer/batter and the background. Therefore, a correct exposure of the golfer/batter results in an overexposure of the sky, which means that the sky may be represented by an almost saturated white color against which a white (and possibly likewise over exposed) ball easily "disappears". Therefore, at least in video recordings/transmissions of some scenes/situations of the game, it is highly desirable to augment the visual impression of the ball.

The U.S. Pat. No. 5,489,099 describes a golf ball tracking apparatus having a video camera for producing data representative of a golf ball, and a video frame processor for determining the golf ball image position within a video frame of the camera. Thereby, the camera may be controlled to automatically follow the movements of the ball, i.e. track the actual flight of the ball through the air.

The U.S. Pat. No. 6,233,007 discloses a solution by means of which it is made possible to track balls, pucks and the like with a camera. Here, empirical color data about the ball is used together with estimated motion vectors to identify a ball trajectory. This, in turn, serves as a basis for following the ball's movements via one or more cameras.

The U.S. Pat. No. 5,953,056 describes a system which enhances the display of a sporting event by tracking a moving ball. Overlay video images are here produced which illustrate the ball path, and the overlay images are successively overlaid a background video image representing the sports scene, such that the viewer easily can follow the ball path.

The U.S. Pat. No. 5,912,700 discloses a system for enhancing the TV presentation of an object (i.e. the ball or puck) in a sporting game, wherein one or more sensors in the object are used. Aided by the sensor(s) a processor associated with the TV camera determines the location of the object, and as a result, the TV signal can be edited or augmented to enhance the presentation of the object.

Although the above-mentioned solutions may improve the viewer's experiences of certain broadcast and/or recorded sporting events important problems remain to be solved in order to render the image enhancement more efficient, reliable and robust. Namely, either an initial manual identification of the ball is required, or sensors/transducers in the ball are required to enable the tracking thereof. However, it may be difficult to accomplish a manual identification with sufficient accuracy within the time available therefore. Moreover, for cost reasons it is generally desirable to reduce the amount of manual intervention as much as possible. On the other hand, any inclusion of sensors or transducers in the ball risk to influence the game itself, at least on a psychological level. Consequently, this is unacceptable, or in any case highly undesirable.

SUMMARY OF THE INVENTION

The object of the present invention is therefore to provide an image enhancing solution, which alleviates the above problems and thus offers a fully automatic acquisition of the ball to be tracked.

According to one aspect of the invention, the object is achieved by the system as initially described, wherein the tracking means is adapted to automatically identify an initial image position for the moving ball. Specifically, for each image in the series of registered source images, the tracking means produces a difference image between the image and an image subsequent thereto. In the difference image all image elements representing a contents alteration below a threshold level are allocated a first value, and all image elements representing a contents alteration above or equal to the threshold level are allocated a second value. The tracking means also identifies a set of ball candidates wherein each ball candidate is represented by a group of neighboring image elements, which all contain the second value and said group fulfills a ball size criterion. Moreover, based on a ball selection algorithm, the tracking means selects the initial image position from the set of ball candidates.

An important advantage of this system is that, without requiring any modification of the ball (i.e. inclusion of sensors etc.), a reliable and robust identification of the moving ball is attained. Based on such identification, the ball path may then be tracked with high accuracy.

According to one preferred embodiment of this aspect of the invention, the system includes a digital processing unit to which the image recording means is connected. The digital processing unit includes the tracking means. The digital processing unit, in turn, may be included in a general-purpose computer, such as a PC. Thereby, a flexible and cost efficient solution is attained. For further cost effectiveness, the digital processing unit may also include the graphics generator.

According to another preferred embodiment of this aspect of the invention, the image recording means includes a main camera and an auxiliary camera. These cameras are co-located and mechanically fixed to one another. Furthermore, the digital processing unit is adapted to accomplish parallax adjustment in respect of the cameras, i.e. to compensate for any differences in view field, optics and resolution, and map each image position recorded by the auxiliary camera to an image position of the main camera (or vice versa). Hence, the image data from the auxiliary camera can be combined correctly with the images registered by the main camera.

According to a further preferred embodiment of this aspect of the invention, the tracking means is adapted to receive a distance parameter to form a basis for the ball selection algorithm. Specifically, the distance parameter reflects a distance between the image recording means and an estimated initial ball position. The parameter determines the ball size criterion, so that for example at a relatively short distance a relatively large ball is expected, and vice versa.

According to yet another preferred embodiment of this aspect of the invention, the tracking means includes a machine interface towards the image recording means. This interface is adapted to receive the distance parameter in the form of a focal distance signal. Hence, the ball size criterion is adjusted automatically. Alternatively, or as a complement thereto, the tracking means may include a user interface, which is adapted to receive a manually entered distance parameter. This can be useful if the image recording means lacks auto focus function, or if the light conditions render such a function unreliable.

According to still another preferred embodiment of this aspect of the invention, the digital processing unit includes a buffer means, which is adapted to buffer images that have been registered by the main camera during a delay period. The digital processing unit is also adapted to generate the synthetic ball trace based on a set of images registered by the auxiliary camera during the delay period. Thereby, the buffer means provides a delay necessary to check whether an identified ball candidate in fact is a ball, and if so, produce the trace.

According to another preferred embodiment of this aspect of the invention, the image recording means includes an image sensor containing an array of sensor elements, for instance of CMOS type (CMOS=Complementary Metal Oxide Semiconductor). This image sensor is adapted to enable read out of image data recorded by a selected sub set of the sensor elements. Hence, the data read-out can be limited to a relevant image area, i.e. that presently is estimated to contain a representation of the ball.

According to still another aspect of the invention the object is achieved by the initially described method, wherein an initial image position for the moving ball is identified automatically by the following. For each image in the series of source images of the scene, a difference image is produced between the image and an image subsequent thereto. In the difference image, all image elements representing a contents alteration below a threshold level are allocated a first value, and all image elements representing a contents alteration above or equal to the threshold level are allocated a second value. Then, a set of ball candidates is identified in which each ball candidate is represented by a group of neighboring image elements that all contain the second value and the group fulfills a ball size criterion, preferably specifying a range of ball image areas. The initial image position for the moving ball is selected from the set of ball candidates based on a ball selection algorithm. Thereby, robust and reliable ball detection is attained.

According to a preferred embodiment of this aspect of the invention, the ball selection algorithm includes a roundness estimation step wherein any ball candidates are discarded which fail to fulfill a rotation symmetry requirement, and/or a requirement pertaining to a relationship between a maximum diameter of the group of neighboring image elements and a combined area of the image elements in the group. Hence, many non-ball artifacts can be eliminated.

According to another preferred embodiment of this aspect of the invention, the ball selection algorithm includes a position estimation step wherein any ball candidates are discarded which are located outside a primary area of the source image. The primary area may represent a lower two-thirds portion of the source image, i.e. in the golf-scene case the image section where the ball is most likely located. Thus, the image processing can be concentrated to where the resources are expected to be most useful.

According to another preferred embodiment of this aspect of the invention, the primary area, additionally or alternatively, represents a 50%-portion of the source image around a central vertical line through the source image. Thereby, the image processing efficiency is further improved.

According to yet another preferred embodiment of this aspect of the invention, the ball selection algorithm implies a stroke estimation procedure wherein the ball candidates in the set of ball candidates are analyzed in three consecutively registered images. The stroke estimation procedure includes the following. A respective path candidate line is defined, which extends straight between each ball candidate in a first registered image and each ball candidate in a third registered image. Each ball candidate is discarded, for which in a second image registered between the first and third registered images, no ball candidate is found within a threshold range from the path candidate line. However, for all other path candidate lines a tentative ball path is defined. Since, normally, only very few path candidate lines fulfill this criterion, the image processing is thereby efficiently focused on the relevant image elements.

According to still another preferred embodiment of this aspect of the invention, the stroke estimation procedure further includes discarding any ball candidate whose tentative ball path has an angle relative to a vertical line exceeding a threshold angle. Namely, irrespective of which sports event that is registered, actual ball paths will only occur at certain angles to the camera orientation. Consequently, all other ball paths may be discarded.

According to another preferred embodiment of this aspect of the invention, the identification of an initial image position for the moving ball is inhibited after that at least one ball has been tracked throughout a first predefined number of images. Thus, for example during the time when a synthetic ball trace is generated in respect of a first ball, the algorithm refrains from searching after a second ball.

According to a further preferred embodiment of this aspect of the invention, after the three consecutively registered images, the tracking involves estimation of a movement vector predicting a ball position in a particular source image. This movement vector is based on: a first image position for the ball in a first source image preceding the particular source image; a second image position for the ball in a second source image subsequent to the first source image however preceding the particular source image; and a third image position for the ball in a third source image subsequent to the second source image however preceding the particular source image. Hence, the ball path is followed steadily during a relatively early tracking phase.

According to yet another preferred embodiment of this aspect of the invention, after an initial second number (>3) of registered images, the ball position in the particular source image is predicted on the basis of a linear relationship between positions for the ball in two images registered immediately prior to the particular image. Hence, in steady state tracking the ball is followed with a minimum of image processing.

According to still another preferred embodiment of this aspect of the invention, the tracking is continued until no ball candidate can be found within a threshold distance from the predicted ball position. Thereby, the tracking is aborted automatically whenever the algorithm fails to track the ball path. Instead, the algorithm then continues to search for a new initial image position for a moving ball.

According to a further aspect of the invention the object is achieved by a computer program, which is directly loadable into the internal memory of a computer, and includes software for controlling the above proposed method when said program is run on a computer.

According to another aspect of the invention the object is achieved by a computer readable medium, having a program recorded thereon, where the program is to control a computer to perform the above proposed method.

Further advantages, advantageous features and applications of the present invention will be apparent from the following description and the dependent claims.

BRIEF DESCRIPTION OF THE DRAWINGS

The present invention is now to be explained more closely by means of preferred embodiments, which are disclosed as examples, and with reference to the attached drawings.

DETAILED DESCRIPTION OF THE DRAWINGS

Figure 1:
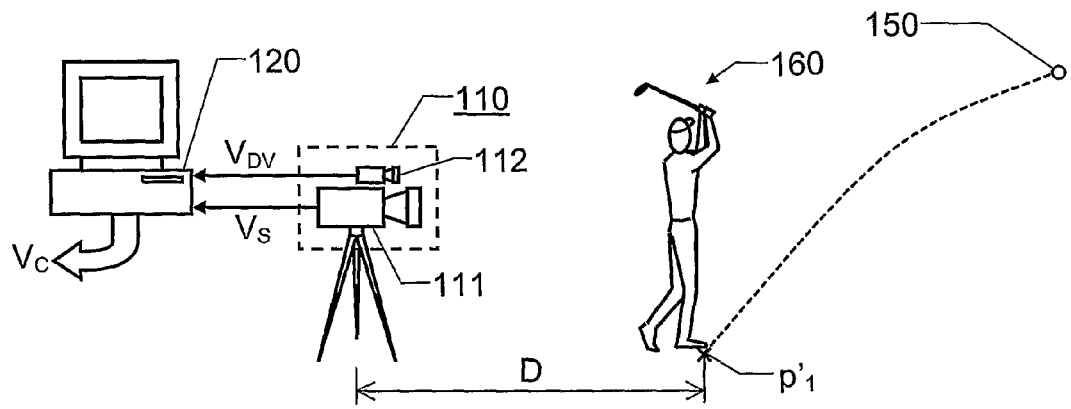
FIG. 1 shows an overview picture of a system according to a first embodiment of the invention and a sportsperson of which images are recorded by the system.

We refer initially to FIG. 1, which shows an overview picture of a system according to a first embodiment of the invention. The FIG. 1 also shows a sportsperson 160 of which a series of images is recorded by the proposed system. Specifically, the system produces a video signal that represents a sports scene wherein a ball 150, during at least a short period, is caused to move in front of an essentially static background. Thus, the scene may include a golfer, a batter or a similar player who performs a ball stroke.

Figure 2:
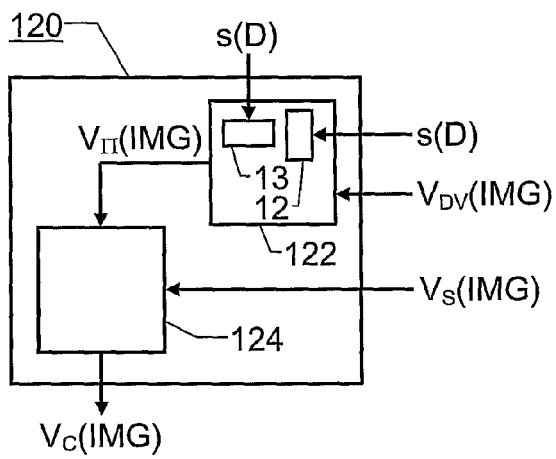
FIG. 2 shows a block diagram over a digital processing unit according to the first embodiment of the invention.

The system includes an image recording means 110, a tracking means and a graphics generator. Preferably, a digital processing unit 120, for instance represented by a PC, implements one or both of the tracking means and the graphics generator. FIG. 2 shows a block diagram over a digital processing unit 120 according to the first embodiment of the invention. The image recording means 110 is adapted to register images of the scene. In a golf implementation it is advantageous if the image recording means 110 is placed and directed such that in one and the same image the golfer, the ball, the hole and the intended ball path all are visible. Thus, if a high stroke is expected, the image recording means 110 should be directed so that the sky occupies a relatively large portion of the image.

It may be preferable to have the digital processing unit 120 physically separated from the image recording means 110, such that e.g. the unit 120 is located in a mixing facility where two or more shots from the same, or a similar, location can be stored and processed jointly. Thus, for example shot comparison is enabled.

The image recording means 110 includes at least one camera for data acquisition, and preferably, a main camera 111 and an auxiliary camera 112 are included. In such a case, the main camera 111 delivers a first series of source images $V_S(IMG)$ of the scene and the auxiliary camera 112 delivers a second series of source images $V_{DV}(IMG)$ of the scene. The main camera 111 may be a TV camera adapted to produce a signal for live transmission, or for recording. The auxiliary camera 112 is preferably digital video camera, e.g. having a CMOS-image sensor, with a relatively high resolution. Moreover, the cameras 111 and 112 are co-located and mechanically fixed to one another, so that they have essentially the same view field.

However, due to differences in the lens optics of the cameras 111 and 112, resolution differences and the fact that the cameras' 111 and 112 image sensors are located at slightly different positions a parallax adjustment is normally necessary to match the first and second series of source images $V_S(IMG)$ and $V_{DV}(IMG)$ to one another. According to a preferred embodiment of the invention, the digital processing unit 120 is adapted to accomplish this parallax adjustment. Moreover, the cameras 111 and 112 may have different frame rates and delays, so that time synchronization is required.

One way to accomplish the parallax adjustment is to aim both the cameras 111 and 112 towards distant and essentially stationary objects. Then, an estimate is made as how much the cameras' images overlap. The overlap is described by means of a function $F_{overlap}$, which reflects a translation from each position (x, y) in a first image of the first series of images to each position (x', y') in a corresponding second image of the second series of images. In order to determine how well the estimate describes the overlap between the images, an absolute difference is calculated between each pixel/image element value of the first image (at position (x, y)) and a corresponding pixel/image element value (i.e. at position (x', y') of the second image. A total sum of all such differences is then calculated as an overall fit, or quality, measure of the function $F_{overlap}$. Then, another overlap estimate is made, and a new total sum of differences is calculated, and so on. An overlap function $F_{overlap}$, associated with a lowest total sum of differences is deemed to describe the parallax relationship between the cameras 111 and 112 sufficiently well.

As a result of the parallax adjustment, synthetic image elements generated on the basis of the second series of source images $V_{DV}(IMG)$ can be combined with the first series of source images $V_S(IMG)$, such that a trace representing the path of the moving ball 150 is shown in the form of successively added image data in a composite image sequence $V_C(IMG)$.

In order to facilitate the tracking of the ball path, it is important that the exposure of the image recording means 110 is regulated appropriately. For example, relevant diaphragms may have to be adjusted manually. Also the exposure time and/or the gain may require modifications to attain an optimal result. Generally, it is advantageous if these parameters are selected such that a brightest non-overexposed picture is accomplished. Namely, overexposed image portions render it difficult to distinguish the ball against the background. The exposure time should be as long as possible without causing excessive movement blur effects. I.e. an exposure time below 2 ms is typically preferred.

The tracking means 122 is adapted to track a path of the moving ball 150 through at least a sub-set of the source images. The tracking performed by the tracking means 122 involves differencing between consecutively registered images. The differencing identifies image areas that have been updated in a later registered image in relation to an earlier registered image. Specifically, for each image in the second series of source images $V_{DV}$(IMG), a difference image is produced between the image and an image subsequent thereto, wherein in the difference image all image elements representing a contents alteration below a threshold level are allocated a first value, e.g. equivalent to black. The remaining image elements (i.e. representing a contents alteration above or equal to the threshold level) are allocated a second value, e.g. equivalent to white. The threshold level is set, such that a moving ball can be expected among these image elements. Moreover, especially in steady state tracking, when the ball's location and size within the image is relatively well known, it is preferable if the threshold level is adaptive. Namely, thereby, the threshold level may automatically attain an appropriate value, for instance, implying that a particular fraction, or number, of the image elements within a certain region shall be allocated the second value.

According to the invention, the tracking means 122 is adapted to automatically identify an initial image position for the moving ball 150 by identifying a set of ball candidates in which each ball candidate is represented by a group of neighboring image elements that all contain the second value. Hence, the set of ball candidates may include a number of white pixel groups, or "blobs". The group must also fulfil a ball size criterion, which will be discussed below. Then, the initial image position is selected from the set of ball candidates based on a ball selection algorithm. Details pertaining to this selection will be described below with reference to FIGS. 5 to 8. Nevertheless, based on the second series of source images $V_{DV}$(IMG), the tracking means 122 produces a ball path signal $V_{\Pi}$(IMG) describing the movements of any ball having been detected throughout at least a sub-set of the images in the second series of source images $V_{DV}$(IMG).

Figure 5:
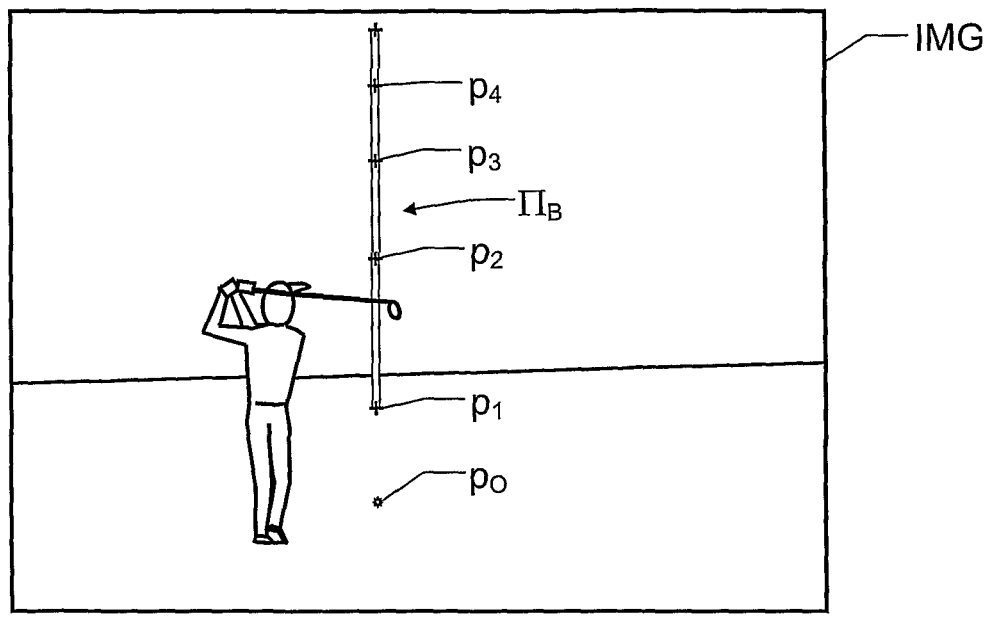
FIG. 5 illustrates how a trace representing the path of a moving ball may be represented in a composite image sequence according one embodiment of the invention.

The graphics generator 124 is adapted to receive the ball path signal $V_{\Pi}$(IMG) and the first series of source images $V_S$(IMG), and in response thereto generate a composite image sequence $V_C$(IMG). The composite image sequence $V_C$(IMG) includes synthetic image elements, which are combined with the images in the first series of source images $V_S$(IMG), such that a trace representing the path of the moving ball 150 is shown in the form of added image data being successively overlaid the image contents of the first series of source images $V_S$(IMG). FIG. 5 shows an image IMG including an example of such a trace $\Pi_B$.

According to one preferred embodiment of the invention, the tracking means 122 is adapted to receive a distance parameter s(D). This parameter forms a basis for the ball selection algorithm by reflecting a distance D between the image recording means 110 and an estimated physical ball position p'$_1$. (i.e. the image representation of where it is deemed most likely that a moving ball occurs).

The distance parameter s(D) determines the ball size criterion, so that a relatively long distance D gives a ball size criterion equivalent to a comparatively small ball, and vice versa, that a relatively short distance D gives a ball size criterion equivalent to a comparatively large ball. According to one preferred embodiment of the invention, the ball size criterion specifies an acceptable ball size interval (equivalent to a ball image area interval). In order to receive the distance parameter s(D), the tracking means 122 includes at least one interface 12 or 13. A machine interface 12 may be included towards the image recording means. Via this interface 12, the distance parameter s(D) can be received automatically in the form of a focal distance signal from an auto focus function in the image recording means 110. Alternatively, or as a complement thereto, the tracking means 122 may include a user interface 13, which is adapted to receive a manually entered distance parameter s(D), i.e. a figure set by the operator of the system.

Figure 3:
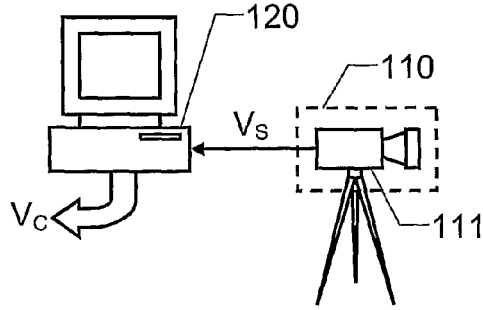
FIG. 3 shows an overview picture of a system according to a second embodiment of the invention.
Figure 4:
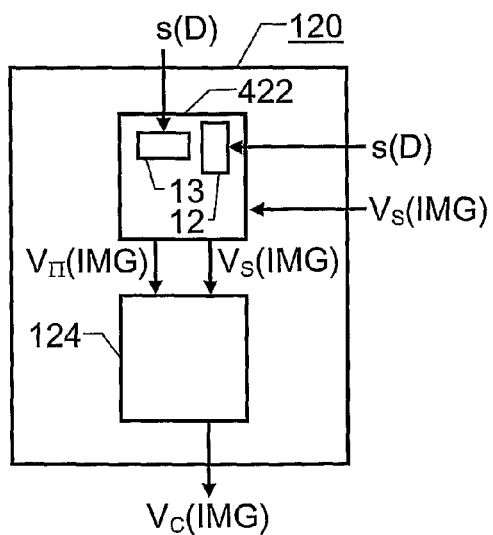
FIG. 4 shows a block diagram over a digital processing unit according to the second embodiment of the invention.

FIGS. 3 and 4 show an overview picture of a system respective a block diagram over the digital processing unit according to a second embodiment of the invention. Here, all reference signs being identical to the reference signs used in the FIGS. 1 and 2 denote the same elements, signals and parameters as described hereinabove with reference to these figures. Thus, in short, the image registering means 110 of the system according to the second embodiment of the invention only includes one camera, for example represented by a TV camera. Consequently, only one series of source images $V_S$(IMG) is produced, and therefore a proposed tracking means 422 is adapted to track a path of the moving ball 150 and generate the ball path signal $V_{\Pi}$(IMG) based on the same images that represent the image contents of the composite image sequence $V_C$(IMG). Otherwise, the operation principle of the tracking means 422 is identical to that of the tracking means 122 in the FIG. 2.

We now turn to FIG. 5 in illustrate how the trace $\Pi_B$ illustrating the path of a moving ball may be represented in a composite image sequence according one embodiment of the invention. In addition to a golfer and a background, the image IMG in FIG. 5 contains synthetic image elements constituting the trace $\Pi_B$, i.e. an augmented ball path image showing the ball's historical positions, essentially since it was struck (or by other means started to move quickly). The trace $\Pi_B$ is generated gradually as the ball moves, such that synthetic image data is added successively and overlaid the image contents of the images in the series of source images (e.g. registered by the main camera 111). Preferably, the color of the trace $\Pi_B$ is allocated adaptively with respect to the background, such that a high contrast is obtained between the trace $\Pi_B$ and the background. Thus, the trace $\Pi_B$ may be white, red, black or have any other suitable color.

According to a preferred embodiment of the invention, the graphics generator 124 is instructed to generate the trace $\Pi_B$ after that the ball position has been successfully tracked throughout a predetermined number of images, say 10. Naturally, in order to enable presentation of the full trace $\Pi_B$ (i.e. from the initial position p$_1$) to the viewers, a certain delay time is required between the incoming series of source images $V_S$(IMG) and $V_{DV}$(IMG) and the outgoing composite image sequence $V_C$(IMG). The delay, in turn, depends on a number of parameters, such as the relevant frame rates of the image recording means 110 and the processing capacity of the tracking means 122 or 422. Nevertheless, a delay of approximately 0.5 s to 1.0 s of the first image sequence $V_S$(IMG) relative to the second image sequence $V_{DV}$(IMG) is generally sufficient to allow the tracking to be performed throughout the predetermined number of images. Of course, thereby the composite image sequence $V_C$(IMG) is also delayed at least as much in relation to the actual sports scene events. However, in most live transmissions this is a fully acceptable delay time.

Either the delay is an effect of the image recording means' 110 technical characteristics (e.g. due to that the auxiliary camera 112 deliver its images earlier than the main camera 111), or an artificial delay must be introduced. This is especially true in case only one camera (i.e. exclusively the main camera 111) is used. Therefore, according to one preferred embodiment of the invention, the digital processing unit 120 includes a buffer means adapted to buffer the images registered by the main camera 111 during a delay period (being equivalent to the predetermined number of images). The digital processing unit 120 is further adapted to generate the trace $\Pi_B$ in respect of at least a sub set of the images registered during the delay period based on a set of images registered either by the auxiliary camera 112 during the delay period (if the image recording means 110 includes two cameras), or based on a set of images registered by the main camera 111 during the delay period (if the image recording means 110 includes only this camera).

In order to ensure that the first and second image sequences $V_S(IMG)$ and $V_{DV}(IMG)$ are synchronized, it is preferable if each image in the respective sequence is time stamped. Moreover, to reflect the ball path appropriately in the composite image sequence $V_C(IMG)$, it is advantageous if the above-described overlap function $F_{overlap}$ is used to translate any ball positions registered by the auxiliary camera 112 to corresponding positions in the images registered by the main camera 111.

In order to reduce the processing load caused by the identification algorithm for automatically detecting a moving ball, the identification of an initial image position $p_1$ for the moving ball is preferably also inhibited after that at least one ball has been tracked throughout a first predefined number of images, say 10, consecutive images.

We assume that before being struck, the ball was stationary (or at least almost stationary) at an original point $p_o$. Then, when the ball is struck, this is detected by the proposed system, and when the ball has reached a position $p_1$, we presume that the ball selection algorithm has concluded that the relevant criteria have been fulfilled, and the trace $\Pi_B$ starts. Naturally, the ball moves (somehow) also between the original point $p_o$ and the position $p_1$. However, this cannot be illustrated by the trace $\Pi_B$, since the original point $p_o$ is not/need not/be known to the system. Therefore, $p_1$ is defined to represent an initial image position for the moving ball. Subsequently, updated ball positions for the moving ball are generated at positions $p_2$, $p_3$ and $p_4$, and so on. However, if desired, it is technically feasible to also extend the trace $\Pi_B$ to an estimated original point $p_o$.

It is should be noted that, even though the FIGS. 1 and 3 show image recording means 110 mounted on tripods, according to the invention, the image recording means 110 may equally well be represented by a hand-carried unit being provided with an image stabilizing means.

Figure 6:
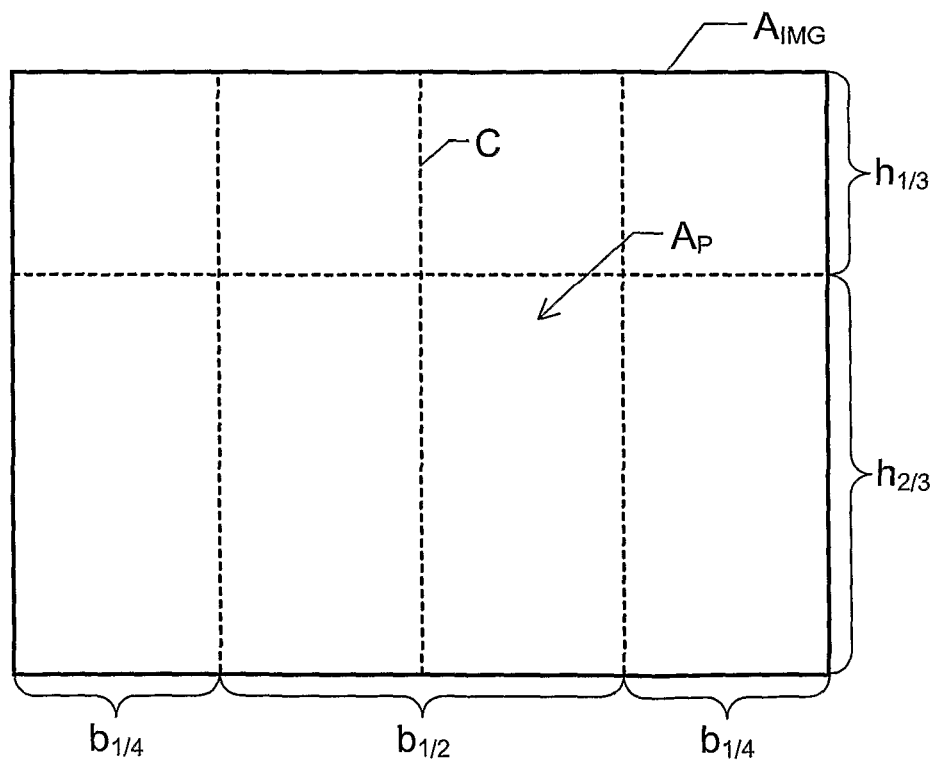
FIG. 6 shows an image area illustrating an estimation step of a proposed ball selection algorithm.

Now, embodiments of an estimation step of the proposed ball selection algorithm will be explained with reference to FIG. 6. Here, a full image area $A_{IMG}$ is shown, which includes a sub-area, a primary area $A_P$, within which the initial image position for the moving ball is expected to be located. Therefore, the ball selection algorithm preferably includes a position estimation step wherein any ball candidates are discarded which are located outside the primary area $A_P$ of the source image.

In the golf case, the primary area $A_P$ may represent a lower two-thirds portion $h_{2/3}$ of the source image's area $A_{IMG}$. The primary area $A_P$ may also, or alternatively, represent a 50%-portion $b_{1/2}$ of the source image around a central vertical line C through the image.

According to one preferred embodiment of the invention, the image recording means 110, say in the auxiliary camera 112, includes an image sensor that contains an array of sensor elements adapted to enable read out of image data recorded by a selected sub set of the sensor elements. Thus, a so-called region of interest (RoI) can be defined, which is equivalent to the primary area $A_P$. Today, for example image sensors of CMOS type exist, which enable such a read-out of image data.

As mentioned previously, the initial image position for the moving ball is selected from the set of ball candidates based on the ball selection algorithm and a ball size criterion. Preferably, this algorithm criterion specifies a range of acceptable ball image areas (i.e. a particular interval of number of image elements), which is derived from the distance parameter s(D).

The ball selection algorithm, in turn, preferably involves a roundness estimation wherein any ball candidates are discarded which fail to fulfill a rotation symmetry requirement, and/or fail to fulfill a requirement pertaining to a relationship between a maximum diameter of the group of neighboring image elements and a combined area of the image elements in the group.

Hence, based on the ball size criterion and the above geometrical criteria, a fair amount of non-balls in the initial set of ball candidates can be discarded. We will now refer to FIGS. 7a and 7b to illustrate further details of the proposed ball selection algorithm according to embodiments of the invention.

Figure 7A:
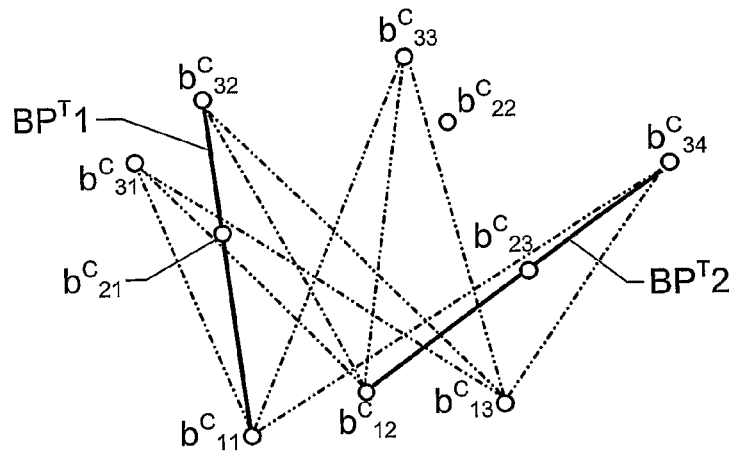
FIGS. 7a, b illustrate further details of the ball selection algorithm according to embodiments of the invention.

The ball selection algorithm implies a stroke estimation procedure wherein the ball candidates in the set of ball candidates are analyzed in three consecutively registered images. FIG. 7a schematically shows a first set of ball candidates $b^c_{11}$, $b^c_{12}$ and $b^c_{13}$ that have been registered in a first image, a second set of ball candidates $b^c_{21}$, $b^c_{22}$ and $b^c_{23}$ that have been registered in a second image and third set of ball candidates $b^c_{31}$, $b^c_{32}$, $b^c_{33}$ and $b^c_{34}$ that have been registered in a third image.

The stroke estimation procedure comprises the following steps. First, a respective path candidate line is defined, which extends straight between each ball candidate $b^c_{11}$, $b^c_{12}$ and $b^c_{13}$ in the first registered image and each ball candidate $b^c_{31}$, $b^c_{32}$, $b^c_{33}$, and $b^c_{34}$ in the third registered image. Then, the procedure investigates, for each path candidate line, whether any of ball candidates $b^c_{21}$, $b^c_{22}$ or $b^c_{23}$ of the second registered image are located within a threshold range from the path candidate line. Each ball candidate is discarded for which no ball candidate is found.

Figure 7B:
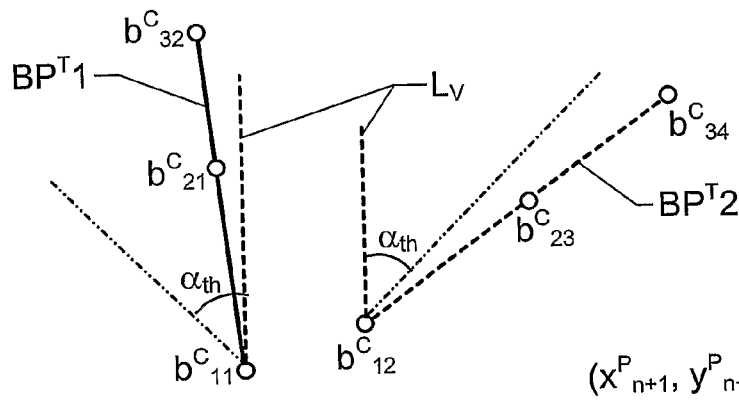

However, a tentative ball path $BP^T1$ and $BP^T2$ is defined for the remaining path candidate lines. The FIG. 7b shows the qualifying tentative ball paths $BP^T1$ and $BP^T2$ of this example. In order to eliminate further false registrations, the stroke estimation procedure may include the following step. In the FIG. 7b two vertical lines $L_V$ are shown, which for illustrative purposes cross the first-image ball candidates $b^c_{11}$ and $b^c_{12}$ respectively of the tentative ball paths $BP^T1$ and $BP^T2$. The tentative ball path $BP^T2$ has an angle relative to the vertical line $L_V$ exceeds a threshold angle $\alpha_{th}$ representing a most angled stroke, which is expected to be possible. In a golf implementation, the threshold angle $\alpha_{th}$ may be around 45°.

Here, the ball candidate described by $b^c_{12}$, $b^c_{23}$ and $b^c_{34}$ is discarded in this step. This leaves us with one remaining moving ball candidate, namely that which is given by $b^c_{11}$, $b^c_{21}$ and $b^c_{32}$. We assume that this candidate embodies a registration of an actual ball, and that as a result the trace $\Pi_B$ representing the path of the moving ball is generated (see FIG. 5). According to one preferred embodiment of the invention, such a trace $\Pi_B$ in the composite image sequence $V_C(IMG)$ is exclusively generated in respect of a ball candidate complying with the ball selection algorithm.

In order to eliminate any further non-balls in the set of ball candidates a requirement may be added to the ball selection algorithm that a second set ball candidates $b^c_{21}$ and $b^c_{23}$ must lie closer to the relevant third set ball candidate $b^c_{32}$ and $b^c_{34}$ respectively than to the relevant first set ball candidate $b^c_{11}$ and $b^c_{12}$ respectively. This is explained by the perspective effect caused by the image recording's position relative to the sportsperson and the direction of the ball path.

Furthermore, the ball selection algorithm may require one or more of the following: that the ball velocity lies within a particular interval (i.e. that the distance between the ball candidate in the first and third sets lies within a certain range); that the ball image area decreases (e.g. the that area in the first set is larger than in the third set, and that the area in the second set is at least larger than half the area in the third set); and that the ball candidate in the third set lies within a certain image area relative to the ball candidate's location in the first set (e.g. if the ball candidate in the first set was found within the lower two-thirds portion of the source image, the ball candidate in the third set must be lie within the upper two-thirds portion of the source image).

Figure 8:
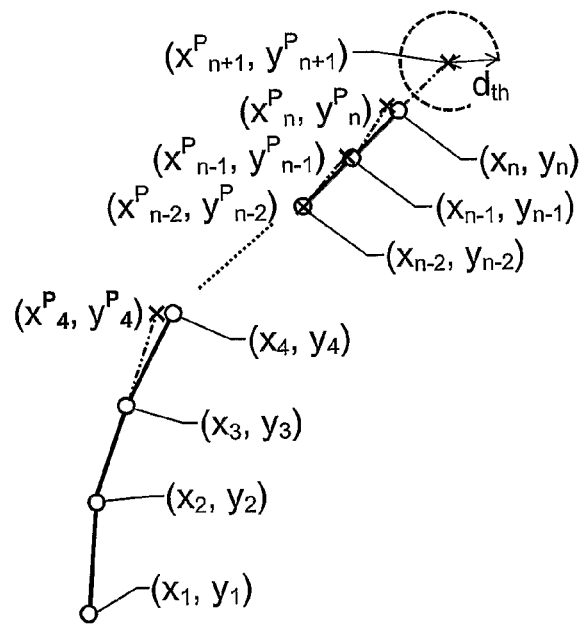
FIG. 8 illustrates certain aspects of a proposed tracking algorithm.

Nevertheless, a ball candidate complying with the ball selection algorithm qualifies to be tracked by the tracking means 122 or 422. FIG. 8 illustrates some aspects of a tracking algorithm performed by the tracking means according to preferred embodiments of the invention. The FIG. 8 shows actual image positions $(x_1, y_1)$, $(x_2, y_2)$, $(x_3, y_3)$, $(x_4, y_4)$, $(x_{n-2}, y_{n-2})$, $(x_{n-1}, y_{n-1})$ and $(x_n, y_n)$ for a ball in a series of images together with a set of estimated ball positions $(x^P_4, y^P_4)$, $(x^P_{n-2}, y^P_{n-2})$, $(x^P_{n-1}, y^P_{n-1})$, $(x^P_n, y^P_n)$ and $(x^P_{n+1}, y^P_{n+1})$ in this series of images.

According to a preferred embodiment of the invention, after that the ball has been tracked in three consecutively registered images, the tracking involves estimation of a movement vector that predicts a ball position in one future image, typically the next image.

Thus, in a particular source image, say a fourth image, the movement vector predicting a ball position $(x^P_4, y^P_4)$ is based on a first image position $(x_1, y_1)$ for the ball in a first source image preceding the particular source image; a second image position $(x_2, y_2)$ for the ball in a second source image subsequent to the first source image however preceding the particular source image; and a third image position $(x_3, y_3)$ for the ball in a third source image subsequent to the second source image however preceding the particular source image.

Specifically, a first movement vector $V_1$ may be calculated as $V_1=(x_2, y_2)-(x_1, y_1)$, and correspondingly a movement second vector $V_2$ may be calculated as $V_2=(x_3, y_3)-(x_2, y_2)$ to reflect the movements between the first and second source images and second and third source images respectively. The predicted ball position $(x^P_4, y^P_4)$ in the fourth image is then calculated as:

$$(x^P_4, y^P_4) = (x_3, y_3) + V_2 \cdot \left(\frac{|V_2|}{|V_1|}\right).$$

Then, in steady state tracking, after an initial second number of registered images (say 10), a ball position in a particular source image is preferably predicted on the basis of a linear relationship between positions for the ball in two images registered immediately prior to the particular image. In the example shown in the FIG. 8, such a predicted ball position $(x^P_n, y^P_n)$ is based on a linear relationship between positions $(x_{n-1}, y_{n-1})$ and $(x_{n-2}, y_{n-2})$ for the ball in the two images registered immediately before the image in which the ball position is predicted. A more reliable measure is attained if the ball position $(x^P_{n+1}, y^P_{n+1})$ in an n+1:th image is predicted according to:

$$(x^P_{n+1}, y^P_{n+1}) = (x^P_n, y^P_n) + V_{n-1} + (V_{n-1} - V_{n-2})$$

where $V_{n-1}=(x_n, y_n)-(x_{n-1}, y_{n-1})$ and $V_{n-2}=(x_{n-1}, y_{n-1})-(x_{n-2}, y_{n-2})$.

Thus, the ball position $(x^P_{n+1}, y^P_{n+1})$ is here based on an absolute velocity alteration between the preceding images rather than a proportional velocity alteration.

As mentioned earlier, certain criteria must be fulfilled before tracking is instigated in respect of a ball candidate and a trace $\Pi_B$ is generated. However, a stop criterion is also required for the ball tracking. Therefore, according to one embodiment of the invention, the tracking is continued until, within 1-3 images, no ball candidate can be found within a threshold distance $d_{th}$ from a predicted ball position $(x^P_{n+1}, y^P_{n+1})$. In the FIG. 8, this is illustrated by means of a dotted circle having the radius $d_{th}$ centered at the predicted ball position $(x^P_{n+1}, y^P_{n+1})$.

Figure 9:
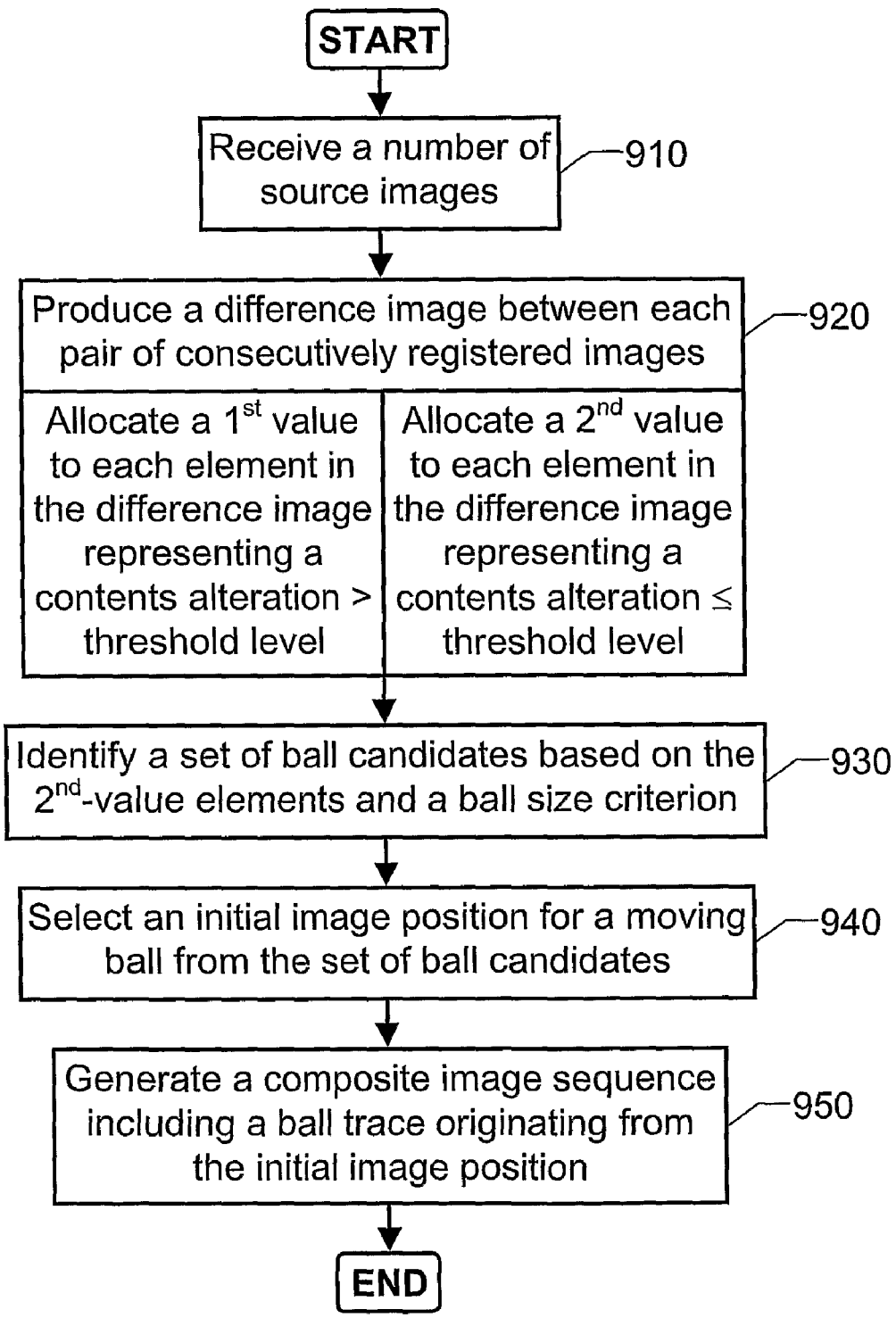
FIG. 9 illustrates, by means of a flow diagram, a general method of controlling a computer apparatus according to the invention.

To sum up, the general method of controlling a computer apparatus to produce a video signal representing a sports scene according to the invention will now be described with reference to the flow diagram in FIG. 9.

An initial step 910 receives a number of consecutive source images of the scene. Then, a step 920, for each image in the series of received images, produces a difference image between the image and an image subsequent thereto. In the difference image all image elements representing a contents alteration below a threshold level are allocated a first value, and all image elements representing a contents alteration above or equal to the threshold level are allocated a second value.

Subsequently, a step 930 identifies a set of ball candidates. Each ball candidate is here represented by a group of neighboring image elements, which all contain the second value. The group must also fulfil a ball size criterion. A following step 940 selects an initial image position for the moving ball based on the set of ball candidates and a ball selection algorithm. Provided that an initial image position for a moving ball is found, a tracking procedure is instigated. A step 950 then generates a composite image sequence wherein synthetic image elements are combined with the source images, such that a trace representing the path of the moving ball from the initial image position is shown in the form of successively added image data.

All of the process steps, as well as any sub-sequence of steps, described with reference to the FIG. 9 above may be controlled by means of a programmed computer apparatus. Moreover, although the embodiments of the invention described above with reference to the drawings comprise computer apparatus and processes performed in computer apparatus, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A system for producing a video signal representing a sports scene wherein, during at least a period, a ball moves in front of an essentially static background, the system comprising:
    an image recording means adapted to register a series of source images of the scene;
    a tracking means adapted to track a path of the moving ball through at least a sub-set of the images in said series, the tracking involving a differencing between consecutively registered images wherein image areas are identified that have been updated in a later registered image in relation to an earlier registered image; and
    a graphics generator adapted to, based on said source images, generate a composite image sequence wherein synthetic image elements are combined with the images in said series, such that a trace representing the path of the moving ball is shown in the form of added image data successively overlaid the image contents of the images in said series,
    wherein the tracking means is adapted to automatically identify an initial image position for the moving ball by:
        producing, for each image in said series, a difference image between the image and an image subsequent thereto, wherein in the difference image all image elements representing a contents alteration below a threshold level are allocated a first value, and all image elements representing a contents alteration above or equal to the threshold level are allocated a second value,
        identifying a set of ball candidates in which each ball candidate is represented by a group of neighboring image elements which all contain the second value and said group fulfills a ball size criterion, and
        selecting the initial image position from the set of ball candidates based on a ball selection algorithm,
        wherein the ball selection algorithm implies a stroke estimation procedure wherein the ball candidates in the set of ball candidates are analyzed in three consecutively registered images, the stroke estimation procedure comprising:
            defining a respective path candidate line extending straight between each ball candidate in a first registered image and each ball candidate in a third registered image,
            discarding each ball candidate for which, in a second image registered between the first and third registered images, no ball candidate is found within a threshold range from the path candidate line, and
            defining a tentative ball path for all other path candidate lines.

2. The system according to claim 1, wherein it comprises a digital processing unit to which the image recording means is connected, and the digital processing unit comprises the tracking means.

3. The system according to claim 2, wherein the digital processing unit comprises the graphics generator.

4. The system according to claim 2, wherein the image recording means comprises a main camera and an auxiliary camera, the cameras are co-located and mechanically fixed to one another, and the digital processing unit is adapted to accomplish a parallax adjustment in respect of said cameras.

5. The system according to claim 1, wherein the tracking means is adapted to receive a distance parameter to form a basis for the ball selection algorithm, the distance parameter reflecting a distance between the image recording means and an estimated initial ball position, and the distance parameter determining the ball size criterion.

6. The system according to claim 5, wherein the tracking means comprises a machine interface towards the image recording means which is adapted to receive the distance parameter in the form of a focal distance signal.

7. The system according to claim 5, wherein the tracking means comprises a user interface adapted to receive a manually entered distance parameter.

8. The system according to claim 4, wherein the digital processing unit comprises a buffer means adapted to buffer images registered by the main camera during a delay period, and
    is adapted to, based on a set of images registered by the auxiliary camera during the delay period, generate the trace in respect of at least a sub set of the images registered during the delay period.

9. The system according to claim 1, wherein the image recording means comprises an image sensor containing an array of sensor elements, and the image sensor is adapted to enable read out of image data recorded by a selected sub set of the sensor elements.

10. A method of producing a video signal representing a sports scene wherein, during at least a period, a ball moves in front of an essentially static background, the method comprising:
    registering a series of source images of the scene;
    tracking a path of the moving ball through at least a sub-set of the images in said series, the tracking involving a differencing between consecutively registered images wherein image areas are identified that have been updated in a later registered image in relation to an earlier registered image; and
    generating, based on said source images a composite image sequence wherein synthetic image elements are combined with the images in said series, such that a trace representing the path of the moving ball is shown in the form of added image data successively overlaid the image contents of the images in said series, wherein the method comprises automatically identifying an initial image position for the moving ball by:
    producing, for each image in said series, a difference image between the image and an image subsequent thereto, wherein in the difference image all image elements representing a contents alteration below a threshold level are allocated a first value, and all image elements representing a contents alteration above or equal to the threshold level are allocated a second value,
    identifying a set of ball candidates in which each ball candidate is represented by a group of neighboring image elements which all contain the second value and said group fulfills a ball size criterion, and selecting the initial image position from the set of ball candidates based on a ball selection algorithm, wherein the ball selection algorithm implies a stroke estimation procedure wherein the ball candidates in the set of ball candidates are analyzed in three consecutively registered images, the stroke estimation procedure comprising:

defining a respective path candidate line extending straight between each ball candidate in a first registered image and each ball candidate in a third registered image, discarding each ball candidate for which, in a second image registered between the first and third registered images, no ball candidate is found within a threshold range from the path candidate line, and defining a tentative ball path for all other path candidate lines.

11. The method according to claim 10, wherein the ball size criterion specifies a range of ball image areas equivalent to a particular interval of image elements.

12. The method according to claim 10, wherein the ball selection algorithm comprises a roundness estimation step wherein any ball candidates are discarded which fail to fulfill at least one of:
a rotation symmetry requirement, and
a requirement pertaining to a relationship between a maximum diameter of the group of neighboring image elements and a combined area of the image elements in the group.

13. The method according to claim 10, wherein the ball selection algorithm comprises a position estimation step wherein any ball candidates are discarded which are located outside a primary area of the source image, the primary area representing a lower two-thirds portion of the source image.

14. The method according to claim 13, wherein the primary area represents a 50%-portion of the source image around a central vertical line through the source image.

15. The method according to claim 10, wherein the stroke estimation procedure further comprises discarding any ball candidate whose tentative ball path has an angle relative to a vertical line exceeding a threshold angle.

16. The method according to claim 10, wherein the method exclusively generates the trace representing the path of the moving ball in the composite image sequence in respect of a ball candidate complying with the ball selection algorithm.

17. The method according to claim 10, wherein the method inhibits the identification of an initial image position for the moving ball after that at least one ball has been tracked throughout a first predefined number of images.

18. The method according to claim 10, wherein, after the three consecutively registered images, the tracking involves estimation of a movement vector predicting a ball position in a particular source image, the movement vector being based on:
a first image position for the ball in a first source image preceding the particular source image;
a second image position for the ball in a second source image subsequent to the first source image however preceding the particular source image; and
a third image position for the ball in a third source image subsequent to the second source image however preceding the particular source image.

19. The method according to claim 18, wherein the method, after an initial second number of registered images, the second number exceeding three, predicts the ball position in the particular source image on the basis of a linear relationship between positions for the ball in two images registered immediately prior to the particular image.

20. The method according to claim 10, wherein the method continues the tracking until no ball candidate can be found within a threshold distance from the predicted ball position.

21. A computer program directly loaded into a internal, non-transitory computer-readable memory of a computer, comprising software comprising computer-readable instructions for:
registering a series of source images of the scene;
tracking a path of the moving ball through at least a sub-set of the images in said series, the tracking involving a differencing between consecutively registered images wherein image areas are identified that have been updated in a later registered image in relation to an earlier registered image; and
generating, based on said source images a composite image sequence wherein synthetic image elements are combined with the images in said series, such that a trace representing the path of the moving ball is shown in the form of added image data successively overlaid the image contents of the images in said series, wherein the method comprises automatically identifying an initial image position for the moving ball by:
producing, for each image in said series, a difference image between the image and an image subsequent thereto, wherein in the difference image all image elements representing a contents alteration below a threshold level are allocated a first value, and all image elements representing a contents alteration above or equal to the threshold level are allocated a second value,
identifying a set of ball candidates in which each ball candidate is represented by a group of neighboring image elements which all contain the second value and said group fulfills a ball size criterion, and
selecting the initial image position from the set of ball candidates based on a ball selection algorithm,
wherein the ball selection algorithm implies a stroke estimation procedure wherein the ball candidates in the set of ball candidates are analyzed in three consecutively registered images, the stroke estimation procedure comprising:
defining a respective path candidate line extending straight between each ball candidate in a first registered image and each ball candidate in a third registered image,
discarding each ball candidate for which, in a second image registered between the first and third registered images, no ball candidate is found within a threshold range from the path candidate line, and
defining a tentative ball path for all other path candidate lines.

22. A non-transitory computer readable medium, having a program recorded thereon comprising computer-readable instructions for:
registering a series of source images of the scene;
tracking a path of the moving ball through at least a sub-set of the images in said series, the tracking involving a differencing between consecutively registered images wherein image areas are identified that have been updated in a later registered image in relation to an earlier registered image; and
generating, based on said source images a composite image sequence wherein synthetic image elements are combined with the images in said series, such that a trace representing the path of the moving ball is shown in the form of added image data successively overlaid the image contents of the images in said series, wherein the method comprises automatically identifying an initial image position for the moving ball by:

producing, for each image in said series, a difference image between the image and an image subsequent thereto, wherein in the difference image all image elements representing a contents alteration below a threshold level are allocated a first value, and all image elements representing a contents alteration above or equal to the threshold level are allocated a second value, identifying a set of ball candidates in which each ball candidate is represented by a group of neighboring image elements which all contain the second value and said group fulfills a ball size criterion, and selecting the initial image position from the set of ball candidates based on a ball selection algorithm, wherein the ball selection algorithm implies a stroke estimation procedure wherein the ball candidates in the set of ball candidates are analyzed in three consecutively registered images, the stroke estimation procedure comprising:

defining a respective path candidate line extending straight between each ball candidate in a first registered image and each ball candidate in a third registered image, discarding each ball candidate for which, in a second image registered between the first and third registered images, no ball candidate is found within a threshold range from the path candidate line, and defining a tentative ball path for all other path candidate lines.

* * * * *